United States Patent
Jeong et al.

(10) Patent No.: US 11,628,240 B2
(45) Date of Patent: Apr. 18, 2023

(54) NON-POLYMERIC TACROLIMUS DRUG-ELUTING STENT AND MANUFACTURING METHOD THEREFOR

(71) Applicants: INDUSTRY FOUNDATION OF CHONNAM NATIONAL UNIVERSITY, Gwangju (KR); CHONNAM NATIONAL UNIVERSITY HOSPITAL, Gwangju (KR)

(72) Inventors: Myung Ho Jeong, Gwangju (KR); Dae Sung Park, Gwangju (KR); In-Ho Bae, Gwangju (KR); Kyung Seob Lim, Gwangju (KR); Jae Won Shim, Gwangju (KR); So Youn Lee, Gwangju (KR); Eun Jae Jang, Gwangju (KR); Doo Sun Sim, Gwangju (KR); In Soo Kim, Gwangju (KR); Jun Kyu Park, Gwangju (KR)

(73) Assignee: INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 0 days.

(21) Appl. No.: 17/046,522

(22) PCT Filed: Dec. 19, 2018

(86) PCT No.: PCT/KR2018/016199
§ 371 (c)(1),
(2) Date: Oct. 9, 2020

(87) PCT Pub. No.: WO2019/198904
PCT Pub. Date: Oct. 17, 2019

(65) Prior Publication Data
US 2021/0170076 A1    Jun. 10, 2021

(30) Foreign Application Priority Data

Apr. 13, 2018    (KR) .................. 10-2018-0043392

(51) Int. Cl.
A61L 31/08    (2006.01)
A61L 24/02    (2006.01)
(Continued)

(52) U.S. Cl.
CPC .......... A61L 31/088 (2013.01); A61F 2/0077 (2013.01); A61F 2/82 (2013.01);
(Continued)

(58) Field of Classification Search
CPC ..................... A61L 2420/02; D01D 5/0084
See application file for complete search history.

(56) References Cited

U.S. PATENT DOCUMENTS 9,795,987 B1 * 10/2017 Park ..................... A61F 2/82
2005/0070996 A1 * 3/2005 Dinh .................. A61L 31/022
623/1.42
(Continued)

FOREIGN PATENT DOCUMENTS

JP    2009530022 A    8/2009
KR    1020050117361 A    12/2005
(Continued)

OTHER PUBLICATIONS

International Search Report from corresponding International Application No. PCT/KR2018/016199, dated Mar. 20, 2019, pp. 1-2, Korean Intellectual Property Office, Daejeon, Republic of Korea.

*Primary Examiner* — Cachet I Proctor
(74) *Attorney, Agent, or Firm* — Hauptman Ham, LLP

(57) ABSTRACT

A tacrolimus drug-eluting stent manufacturing method according to the present invention enables a tacrolimus drug to be strongly and stably bound onto a stent, while also not
(Continued)

necessarily involving a separate step of introducing a surface-binding functional group for the binding of a drug onto a stent and a step of introducing, into the drug, a functional group capable of binding to the surface-binding functional group, and a tacrolimus drug-eluting stent manufactured by the manufacturing method has a greater total drug elution amount and has a more excellent delayed drug-elution property.

6 Claims, 3 Drawing Sheets

(51) Int. Cl.
 *A61F 2/00* (2006.01)
 *A61F 2/82* (2013.01)
 *A61K 31/436* (2006.01)
 *B23K 26/352* (2014.01)
 *C23C 16/30* (2006.01)
 *B23K 26/0622* (2014.01)

(52) U.S. Cl.
 CPC ........ *A61K 31/436* (2013.01); *B23K 26/0624* (2015.10); *B23K 26/352* (2015.10); *C23C 16/308* (2013.01); *A61F 2002/0086* (2013.01); *A61F 2240/002* (2013.01); *A61F 2250/0068* (2013.01); *A61L 2300/416* (2013.01); *A61L 2420/02* (2013.01); *A61L 2420/08* (2013.01)

(56) References Cited

U.S. PATENT DOCUMENTS

| | | | | |
|---|---|---|---|---|
| 2008/0071355 | A1* | 3/2008 | Weber | A61L 31/10 623/1.42 |
| 2009/0030504 | A1* | 1/2009 | Weber | A61L 31/16 623/1.42 |
| 2011/0009954 | A1* | 1/2011 | Cho | A61L 31/022 623/1.42 |
| 2012/0141656 | A1* | 6/2012 | Orr | B05D 1/04 118/620 |

FOREIGN PATENT DOCUMENTS

| | | |
|---|---|---|
| KR | 1020110005058 A | 1/2011 |
| KR | 101046674 B1 | 7/2011 |
| KR | 101653535 B1 | 9/2016 |
| KR | 101786020 B1 | 10/2017 |

* cited by examiner

[FIG. 1]
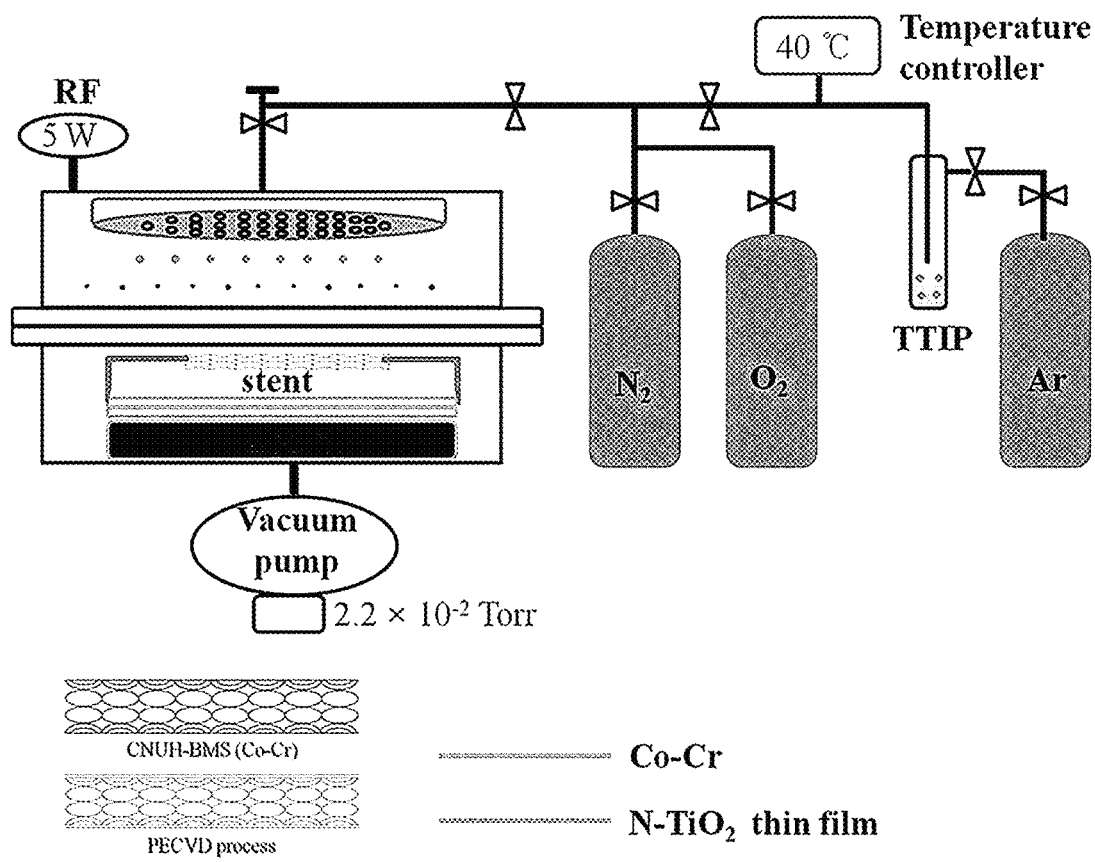
[FIG. 2]
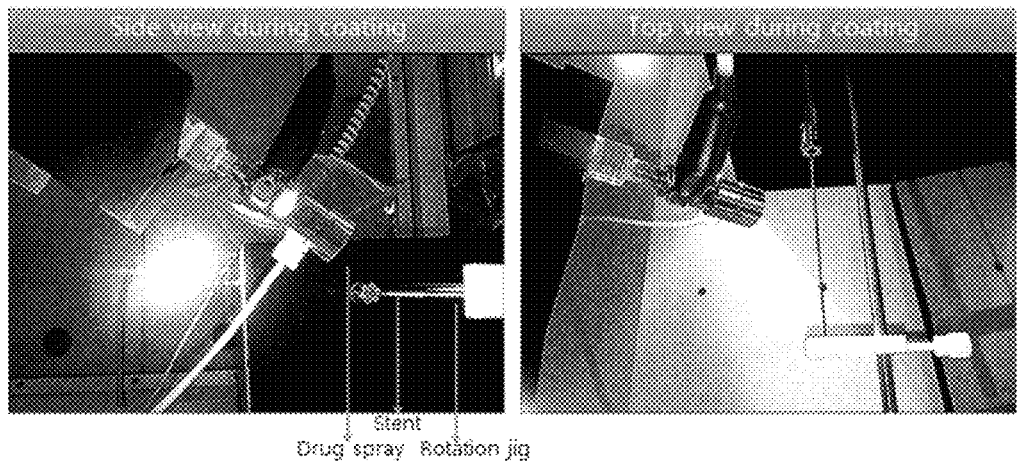

[FIG. 3]
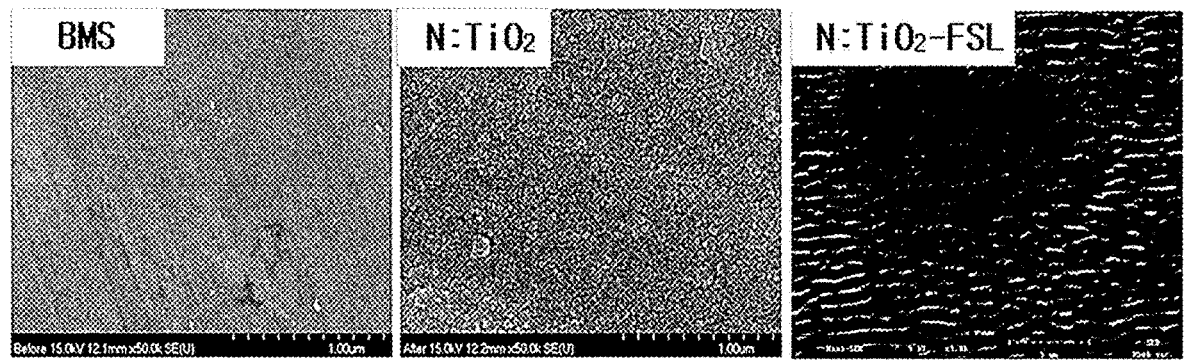
[FIG. 4]
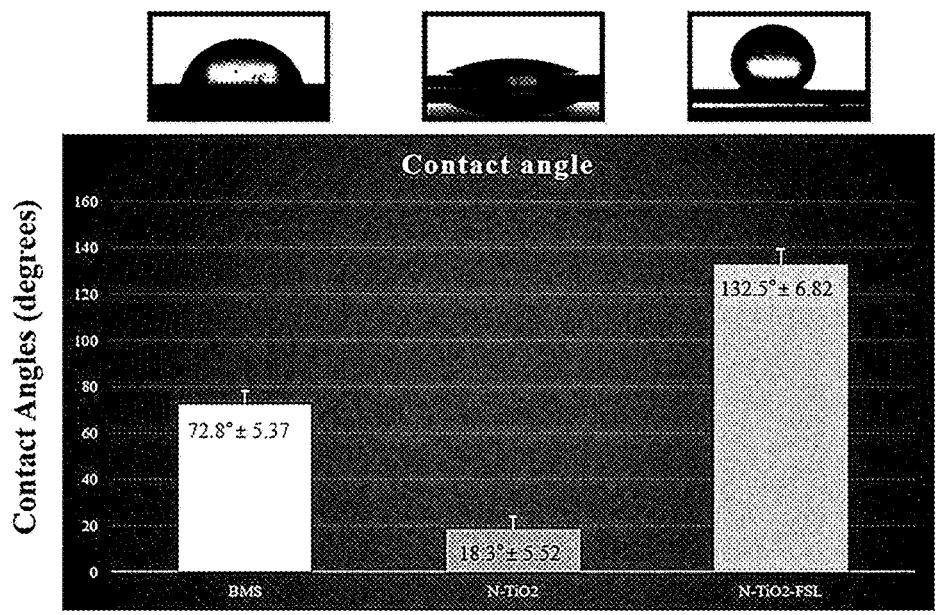

[FIG. 5]
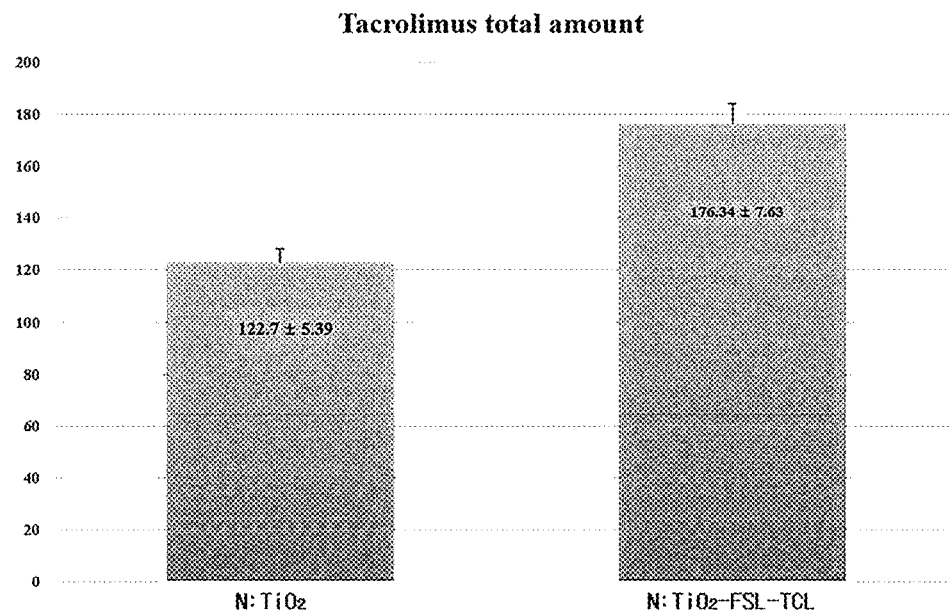
[FIG. 6]
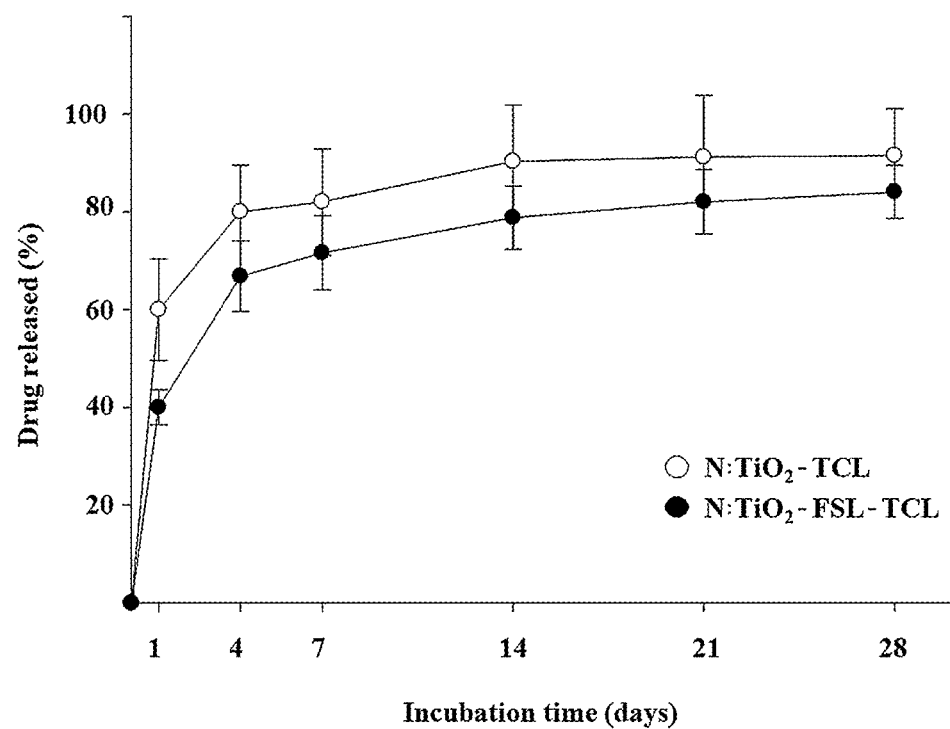

NON-POLYMERIC TACROLIMUS DRUG-ELUTING STENT AND MANUFACTURING METHOD THEREFOR

TECHNICAL FIELD

The present invention relates to a tacrolimus drug-eluting stent and a manufacturing method thereof.

BACKGROUND ART

A vascular stent is a medical appliance which, when a blood vessel becomes narrower due to various diseases occurring in the human body to cause bad blood circulation, is placed inside the blood vessel to dilate the vessel. Therefore, a material forming the stent is required to have not only mechanical physical properties such as flexibility for inserting the stent into a complex and curved blood vessel during operation, but also, in particular, high biocompatibility and stability to the human body.

However, after a certain period of time after stent treatment, blood clots and fat are accumulated again in a stent lumen to cause restenosis often. In the past, as a method for inhibiting vascular restenosis, a drug-eluting stent (DES) which is coated with a small amount of drug which may inhibit cell differentiation and constantly releases the drug, has been developed. A representative example of the drug-eluting stent includes drug-eluting stents using a polymer such as a drug-eluting stent coated with paclitaxel (paclitaxel-eluting stent, TAXUS™), a stent releasing sirolimus which is a immunosuppressant (sirolimus-eluting stent, Cypher™), and a stent releasing everolimus (everolimus-eluting stent, XIENCE PRIME, Abbott), but problems to be overcome such as inflammation and late thrombosis due to use of the polymer still remain.

As a technology for solving the problems, Korean Patent Registration Publication No. 10-1653535 discloses a polymer-free everolimus vascular drug-eluting stent using an electrospinning technique. Specifically, the patent document discloses that the vascular drug-eluting stent is coated with a drug by electrospinning without using a polymer, thereby precisely controlling a total content of a everolimus-based drug bound thereto, even without using a polymer which may cause late thrombosis, and may form a uniform layer.

However, the patent document has a limitation in that a process of introducing a surface-binding functional group is essentially involved so that the drug is bound onto the stent when manufacturing the stent, and a process of introducing a functional group capable of binding to the surface-binding functional group into the drug is essentially involved.

Accordingly, a study of a manufacturing method of stent in which a process of introducing a separate surface-binding functional group for binding a drug onto a stent and a process of introducing a functional group capable of binding to the surface-binding functional group to a drug are not essentially involved, while the drug may be strongly and stably bound onto a stent, is needed. Besides, a study of a stent having a large total drug elution amount of the stent and excellent drug elution delay and a manufacturing method thereof is needed.

DISCLOSURE

Technical Problem

An object of the present invention is to provide a tacrolimus drug-eluting stent in which a process of introducing a separate surface-binding functional group for binding a drug onto a stent and a process of introducing a functional group capable of binding to the surface-binding functional group to a drug are not essentially involved, while the drug may be strongly and stably bound onto a stent, and a manufacturing method thereof.

Another object of the present invention is to provide a tacrolimus drug-eluting stent having a larger total drug elution amount of the stent and better drug elution delay and a manufacturing method thereof.

Technical Solution

In one general aspect, a manufacturing method of a tacrolimus drug-eluting stent includes: a) forming a nitrogen-doped titanium oxide layer on a stent surface, b) irradiating the titanium oxide layer with a femtosecond pulse laser to perform femtosecond laser processing, and c) electrospinning an electrospinning mixed solution including a tacrolimus drug and a solvent on the femtosecond laser-processed titanium oxide layer.

In an exemplary embodiment of the present invention, in step a), the titanium oxide layer may have an average thickness of 0.2 to 2 µm.

In an exemplary embodiment of the present invention, in step c), a first solvent and a second solvent may have a boiling point difference of 25° C. or more and each boiling point of the two solvents may be 120° C. or less.

In an exemplary embodiment of the present invention, in step c), the first solvent may have a boiling point lower than that of the second solvent and a weight ratio of the first solvent to the second solvent may be 100:30 to 80.

In an exemplary embodiment of the present invention, in step c), the electrospinning mixed solution may not include a polymer.

In an exemplary embodiment of the present invention, in step b), the femtosecond laser-processed titanium oxide layer may satisfy the following Relation 1. In the following Relation 1, $\theta_F$ is a water contact angle to the femtosecond laser-processed titanium oxide layer and $\theta_0$ is a water contact angle to the femtosecond laser-unprocessed titanium oxide layer.

$$\theta_F/\theta_0 \geq 5 \quad \text{[Relation 1]}$$

The tacrolimus drug-eluting stent according to an exemplary embodiment of the present invention may satisfy the following Relation 2. In the following Relation 2, $R_{7d}$ is a cumulative elution amount of a drug which has been eluted by the drug-eluting stent at 37° C. and 100 rpm for 7 days in a phosphate buffer saline solvent at pH 7.4, $R_A$ is a total loading amount of the drug loaded on the stent, and the unit of the cumulative elution amount and the total loading amount is a mass unit.

$$R_{7d}/R_A \leq 0.75 \quad \text{[Relation 2]}$$

The tacrolimus drug-eluting stent according to an exemplary embodiment may satisfy the following Relation 3: In the following Relation 3, $R_{1d}$ is a cumulative elution amount of a drug which has been eluted by the drug-eluting stent at 37° C. and 100 rpm for 1 day in a phosphate buffer saline solvent at pH 7.4, $R_A$ is a total loading amount of the drug loaded on the stent, and the unit of the cumulative elution amount and the total loading amount is a mass unit.

$$R_{1d}/R_A \leq 0.45 \quad \text{[Relation 3]}$$

Advantageous Effects

The manufacturing method of a tacrolimus drug-eluting stent according to the present invention does not essentially involve a process of introducing a separate surface-binding functional group for binding a drug onto a stent and a process of introducing a functional group capable of binding to the surface-binding functional group to a drug, while allowing the drug to be strongly and stably bound onto a stent.

In addition, the tacrolimus drug-eluting stent manufactured by the manufacturing method of the present invention has a larger total drug elution amount of the stent and better drug elution delay.

The effects described in the specification which are expected by the technical features of the present invention and the intrinsic effects are regarded as being described in the specification of the present invention, though the effects are not explicitly mentioned in the present invention.

DESCRIPTION OF DRAWINGS

FIG. 1 is a process schematic diagram of chemical vapor deposition used in a process of forming a nitrogen-doped titanium oxide layer, in Example 1.

FIG. 2 is images at the time of electrospinning of a drug coating process using electrospinning, in Example 1.

FIG. 3 is scanning electron microscope (SEM) images for an initial stent (BMS), a stent ($N:TiO_2$) coated with a nitrogen-doped titanium oxide layer, and a stent ($N:TiO_2$-FSL) in which femtosecond laser processing was performed on a nitrogen-doped titanium oxide layer, in Example 1.

FIG. 4 shows results of measuring each of water contact angles to the surfaces of the initial stent (BMS), the stent ($N:TiO_2$) coated with a nitrogen-doped titanium oxide layer, and a stent ($N:TiO_2$-FSL) in which femtosecond laser processing was performed on a nitrogen-doped titanium oxide layer, in Example 1.

FIGS. 5 and 6 show results of measuring a total tacrolimus loading amount and an elution delay characteristic of the tacrolimus drug-eluting stent ($N:TiO_2$-FSL-TCL) manufactured in Example 1.

BEST MODE FOR CARRYING OUT THE INVENTION

Hereinafter, a non-polymeric tacrolimus drug-eluting stent and a manufacturing method thereof will be described in detail, with reference to the accompanying drawings.

The drawings illustrated in the present specification are provided by way of example so that the idea of the present invention may be sufficiently conveyed to a person skilled in the art. Therefore, the present invention is not limited to the provided drawings, but may be embodied in many different forms, and the drawings may be exaggerated in order to clear the spirit of the present invention.

Technical terms and scientific terms used in the present specification have the general meaning understood by those skilled in the art to which the present invention pertains unless otherwise defined, and a description for the known function and configuration obscuring the gist of the present invention will be omitted in the following description and the accompanying drawings.

The singular form of the term used herein may be intended to also include a plural form, unless otherwise indicated.

The terms referring each step such as s1, s2, s3, . . . ; a1, a2, a3, . . . ; b1, b2, b3, . . . ; and a, b, c, . . . mentioned in the present specification themselves are only used for indicating any step, means, or the like, and are not construed as meaning an order relation of each object referred by the terms.

The unit of % used herein without particular mention refers to % by weight, unless otherwise defined.

MODE FOR CARRYING OUT THE INVENTION

As a result of repeating great deal of effort for improving problems which are essentially involved in a process of introducing a surface-binding functional group so that a drug may be stably bound onto the stent, due to not using a polymer and a process of introducing a functional group capable of binding to the surface-binding functional group to a drug, in a conventional manufacturing method of a stent by coating with a drug using electrospinning, the present inventor found that when a tacrolimus drug is used, femtosecond laser processing is performed between a process of forming a nitrogen-doped titanium oxide layer and a process of binding the tacrolimus drug by electrospinning, so that the problems are solved without using a polymer, of course, and a total drug elution amount of the stent is increased and drug elution delay is better, thereby completing the present invention.

The manufacturing method of a tacrolimus drug-eluting stent according to the present invention includes: a) forming a nitrogen-doped titanium oxide layer on a stent surface, b) irradiating the titanium oxide layer with a femtosecond pulse laser to perform femtosecond laser processing, and c) electrospinning an electrospinning mixed solution including a tacrolimus drug and a solvent on the femtosecond laser-processed titanium oxide layer.

Step a) is a step of forming a nitrogen-doped titanium oxide layer on a stent surface. Specifically, in the step a), a method of forming a nitrogen-doped titanium oxide layer on a stent surface may be performed using known various methods, and for example, may include various methods such as chemical vapor deposition, dip coating, physical vapor deposition, and aerosol deposition.

As a preferred example, in the step a), the method of forming a nitrogen-doped titanium oxide layer on a stent surface may be chemical vapor deposition (plasma enhanced chemical vapor deposition, PECVD). When the chemical vapor deposition is used, a more uniform layer may be formed. In addition, thereafter, a finally manufactured stent through femtosecond laser processing of step b) and a tacrolimus drug binding process by electrospinning of step c) may be induced to have a more uniform layer formed on an outermost surface.

As a more specific example, the step a) may include reacting a titanium precursor, a nitrogen gas, and an oxygen gas using chemical vapor deposition to form a nitrogen-doped titanium oxide layer on the stent surface. The titanium precursor may be any material to form the titanium oxide layer, and for example, may include any one or two or more selected from titanium butoxide, tetraethylmethylamino titanium, titanium ethoxide, titanium isopropoxide (titanium (IV) isopropoxide), tetramethylheptadiene titanium, and the like. A reaction temperature may be 300 to 600° C., and a discharge voltage may be 1 to 300 W. Here, an inert gas such as argon may be used as a carrier gas, and a flux ratio of an argon gas, an oxygen gas, and a nitrogen gas may be 100:5 to 30:1 to 10, respectively. However, a coating method of the nitrogen-doped titanium oxide layer described above is only described as a specific example, and the present invention is not limited thereto, of course.

When the titanium oxide layer is formed on the stent surface using chemical vapor deposition in the step a), an average thickness to be formed of the titanium oxide layer may be in a range of 0.05 to 2 μm, preferably in a range of 0.2 to 2 μm, and more preferably in a range of 0.5 to 1.8 μm. When these ranges are satisfied, a total drug loading amount and a drug elution delay characteristic of the finally manufactured stent are significantly improved. Specifically, since a value of the lower limit of the range or more is satisfied, thereafter, a fatal problem that a titanium oxide layer structure collapses by the femtosecond laser processing of step b) may be prevented, thereby securing structure stability by femtosecond laser irradiation. Therefore, a total loading amount of tacrolimus and the elution delay characteristic of tacrolimus is further improved. Besides, a fatal problem that even after a long period of time has passed after manufacture or during use, a drug elution effect is rapidly decreased, so that the drug effect is substantially not shown, may be minimized. Also, a total content of the drug bound onto the nitrogen-doped titanium oxide layer may be precisely controlled, so that the total content of the drug and a delay degree may be calculated according to a required purpose to manufacture a stent. Then, since a value of the upper limit of the range or more is satisfied, problems such as decreased flexibility of a stent and delamination of the titanium oxide layer may be minimized.

Here, since a deposition reaction time is a time taken until a target average thickness is obtained and may be appropriately adjusted, the time is not largely limited and for example, may be 1 to 10 hours. However, this has been described as a specific example, and the present invention is not limited thereto, of course.

The nitrogen-doped titanium oxide layer may be a coating layer of for example, a compound in the form of $TiO_{2-x}N_x$ formed on the stent surface, wherein X may be in a range of 0.001 to 1. A crystal structure of the titanium oxide layer is not largely limited, and may have various crystal structures, for example, rutile, anatase, brookite, and the like. However, this has been described as a preferred example, and since it is a widely known technique to form the nitrogen-doped titanium oxide layer on a stent, various literatures may be referred to, and the present invention is not limited thereto, of course.

Various stents known in the art may be used as the stent, and the properties such as material, shape, length, and weight may be appropriately adjusted by a person skilled in the art, and thus, the stent may be freely selected. Specifically, the stent material may be a biocompatible metal known in the art, a metal of various components bound onto the biocompatible metal, or the like. It is preferred that the stent material has elasticity so as to have excellent motility, has no corrosiveness, and is harmless to the human body. For example, the material may include a biocompatible metal including any one metal selected from stainless steel, nitinol, tantalum, platinum, titanium, cobalt, chromium, molybdenum, and the like or an alloy of two or more thereof. As a specific and preferred example, the stent material may include cobalt, chromium, or an alloy thereof. A specific example of a stent type is known in Korean Patent Laid-Open Publication No. 10-2000-0069536, Korean Patent Laid-Open Publication No. 10-1999-0035927, Korean Patent Laid-Open Publication No. 10-1999-0087472, Korean Patent Laid-Open Publication No. 10-2002-0093610, Korean Patent Laid-Open Publication No. 10-2004-0055785, and the like, and thus, these references may be referred to.

The step b) is a step of irradiating the nitrogen-doped titanium oxide layer coated on the stent surface with a femtosecond pulse laser. By irradiating the nitrogen-doped titanium oxide layer with the femtosecond pulse laser, micropores and/or fine irregularities may be formed on the titanium oxide layer, and thus, in the electrospinning of step c) later, the total drug loading amount may be further increased and the drug elution delay characteristic of the finally manufactured stent may be improved.

Since a surface modification using irradiation of the femtosecond pulse laser itself is a known technique, these known references may be referred to. As a specific example, power may be 2 to 10 W, a wave length may be 500 to 2,000 nm, a focal length may be 20 to 70 mm, a working distance may be 20 to 50 mm, a numerical aperture may be 0.1 to 0.2, and a depth of focus may be 10 to 20 μm. However, this has been described as a specific embodiment example, and the present invention is not limited thereto, of course.

In the step b), when the nitrogen-doped titanium oxide layer is irradiated with the femtosecond pulse laser, hydrophobicity improvement and surface roughness are imparted to the irradiated surface layer, and then drug binding by electrospinning in step c) may be further improved.

Specifically, in the step b), the femtosecond laser-processed titanium oxide layer may satisfy the following Relation 1. In the following Relation 1, $\theta_F$ is a water contact angle to the femtosecond laser-processed titanium oxide layer and $\theta_0$ is a water contact angle to the femtosecond laser-unprocessed titanium oxide layer.

$\theta_F/\theta_0 ≥ 5$    [Relation 1]

The step c) is a step of electrospinning a tacrolimus drug on the femtosecond laser-processed nitrogen-doped titanium oxide layer to bind the tacrolimus drug to the titanium oxide layer. In general, since the drug is not strongly bound and has a low binding stability degree by a conventional physical coating method such as dip coating, there are limitations in that a drug release characteristic is significantly decreased and a release duration is also very short. However, when the tacrolimus drug is electrospun on the titanium oxide layer treated with the femtosecond laser in step b), it is not necessary to essentially involve a process of introducing a separate surface-binding functional group performed on the titanium oxide layer and to essentially involve an additional process of introducing a functional group capable of binding to the surface-binding functional group to the drug. Thus, as the femtosecond laser processing and the tacrolimus drug are used on the titanium oxide layer in step b), binding between the drug and the titanium oxide layer is in the state of being stronger and stabler, even without additional processes such as a process of introducing the surface-binding functional group and a process of introducing a functional group to the drug. Besides, binding of the drug by electrospinning may form a more uniform layer as compared with a physical method such as dip coating. Therefore, a drug release amount may be maintained more constantly.

Since the electrospinning method itself is a known technique, known literatures may be referred to. As a specific example, the electrospinning method of step c) may be a method of spinning a drug mixture including an everolimus-base drug and a solvent on a femtosecond laser-processed nitrogen-doped titanium oxide layer using a high voltage generator. In some cases, the mixture may further include any one or more accelerators selected from 4-dimethylaminopyridine (DMAP), 1-(3-dimethylaminopropyl)-3-ethyl carbodiimide (DAEC), and the like. Here, an applied voltage may be 1 to 15 kV, an air pressure may be 1 to 10 kgf/cm², a distance from a nozzle to a stent may be 10 to 15 cm, a stent rotation speed may be 50 to 100 rpm, a spray speed may be 30 to 90 μl/min, and the like. However, these are only specific examples, and the present invention is not limited thereto, of course.

The solvent may be various kinds of solvents, but preferably may be cosolvents including different kinds of solvents from each other having a boiling point difference from each other of 25° C. or more, and more preferably, the boiling points of the solvents are all 120° C. or less, in terms of minimizing a decreased drug loading content and a decreased drug elution delay characteristic due to decreased volatility. Since a lower limit of the boiling point of the solvent may be such that the solvent is present as a liquid phase, the boiling point may be higher than a temperature during the electrospinning. When cosolvents including a first solvent and a second solvent having a boiling point of 120° C. or less and a boiling point difference each other of 25° C. or more are used as the solvent of the drug during the electrospinning, the total drug loading amount and the drug elution delay characteristic are further improved. When the stent is coated with the drug, the solvent used with the drug affects a loading mechanism of the drug, and specifically, solvent volatility affects the total drug loading amount and the drug elution characteristic. In particular, when the cosolvents including two or more solvents of a solvent having excellent volatility and a solvent having relatively low volatility are used as a solvent of the drug in the electrospinning on the femtosecond laser-processed nitrogen-doped titanium oxide layer of the stent, an effect of further improving the drug elution delay characteristic is implemented. For example, when the cosolvents are used as the solvent of the drug in the electrospinning on a femtosecond laser-unprocessed nitrogen-doped titanium oxide layer, the effect of further improving the drug elution delay characteristic may not be substantially implemented.

A specific example of the solvent may be any one or two or more selected from acetonitrile, toluene, acetone, benzene, butanone, tetrahydrofuran, methanol, ethanol, chloroform, and the like. A more specific example may be acetonitrile, acetone, and the like as the first solvent and toluene, benzene, and the like as the second solvent. However, these have been only described as a preferred example, and since the solvent may be appropriately selected considering the boiling point of the solvent as described above, the present invention should not be limitedly construed as the kinds of solvents described above.

When the solvent is the cosolvents, the cosolvents include the first solvent and the second solvent, and assuming that the first solvent has a lower boiling point than the second solvent, a weight ratio of the first solvent and the second solvent is not largely limited, but it is preferred that the content of the first solvent having a lower boiling point is higher, and for example, the weight ratio is 100:30 to 80 is more preferred. When this is satisfied, the effect of further improving the total drug loading amount and the drug elution delay characteristic may be better implemented.

The tacrolimus drug-eluting stent manufactured by the manufacturing method according to the present invention may be manufactured without including a polymer, and specifically, the effects described above are implemented even without using a polymer in the drug coating in the step c). However, this is for describing the effects as advantages of the present invention, and a polymer may be included in the stent according to the present invention, and even when a polymer is further used in the drug coating in the step c), the effects according to the present invention described above are implemented as they are, and thus, it should not be limitedly construed that the use of a polymer is excluded from the stent according to the present invention.

In an example of the present invention, the manufacturing method of the vascular drug-eluting stent may further include separating and washing the stent after the step c). For example, the step may be a step of washing the stent with an organic solvent of alcohols and with tertiary distilled water several times, and then a drying step may be further performed. The washing step and the drying step may be performed according to the known washing method and drying method which may be carried out by a person skilled in the art, and thus, are not limited.

As described above, the tacrolimus drug-eluting stent according to the present invention has an excellent tacrolimus drug elution delay characteristic.

Specifically, the tacrolimus drug-eluting stent according to an exemplary embodiment of the present invention has an excellent initial drug elution delay characteristic after manufacturing, and may satisfy the following Relation 2. In the following Relation 2, $R_{7d}$ is a cumulative elution amount of a drug which has been eluted by the drug-eluting stent at 37° C. and 100 rpm for 7 days in a phosphate buffer saline solvent at pH 7.4, $R_A$ is a total loading amount of the drug loaded on the stent, and the unit of the cumulative elution amount and the total loading amount is a mass unit.

$$R_{7d}/R_A \leq 0.75 \quad \text{[Relation 2]}$$

In addition, the tacrolimus drug-eluting stent according to an exemplary embodiment of the present invention has an excellent mid drug elution delay characteristic after manufacturing, and may satisfy the following Relation 3. In the following Relation 3, $R_{1d}$ is a cumulative elution amount of a drug which has been eluted by the drug-eluting stent at 37° C. and 100 rpm for 1 day in a phosphate buffer saline solvent at pH 7.4, $R_A$ is a total loading amount of the drug loaded on the stent, and the unit of the cumulative elution amount and the total loading amount is a mass unit.

$$R_{1d}/R_A \leq 0.45 \quad \text{[Relation 3]}$$

Specific test conditions of Relation 2 and Relation 3 may be those of an elution measurement test performed at a rotation speed of 100 rpm and an elution temperature of 37° C. in a phosphate buffer saline (PBS) at pH 7.4. Here, an absorbance may be measured at 213 nm using high performance liquid chromatography (HPLC) or the like and calculated. More specific test conditions may be in accordance with an elution test method of Japanese Pharmacopoeia.

Hereinafter, the present invention will be described in detail by the Examples, however, the Examples are for describing the present invention in more detail, and the scope of the present invention is not limited to the following Examples.

Example 1

<Process of Forming Nitrogen-Doped Titanium Oxide Layer>

In order to form a nitrogen-doped titanium oxide layer on a stent surface, a Co—Cr alloy stent (BMS) surface was coated with the nitrogen-doped titanium oxide layer using chemical vapor deposition by the following method, thereby manufacturing a stent (N:TiO$_2$) coated with a titanium oxide layer.

Specifically, as shown in FIG. 1, a Co—Cr alloy stent was fixed to a vacuum chamber ($2.2 \times 10^{-2}$ torr) connected to a radio frequency (RF) plasma generator which generates plasma and a vacuum pump using a titanium wire, and a temperature of the plasma chamber was maintained at 400° C. Then, an argon gas (high purity Ar gas, Azusanso, 99.999%) was used as a carrier gas and titanium isopropoxide (titanium(IV) isopropoxide, 97%, Sigma-Aldrich Co.) was used as a precursor. Here, an oxygen gas and a nitrogen gas (high purity $O_2/N_2$) were reacted to coat the Co—Cr alloy stent surface with the nitrogen-doped titanium oxide layer. At this time, a flow rate of the argon gas was 100 sccm, the flow rate of the oxygen gas was 16 sccm, and the flow rate of the nitrogen gas was 4 sccm, and the reaction was performed with a discharge power of 5 W until an average thickness of the nitrogen-doped titanium oxide layer is 1 μm.

<Femtosecond Laser Processing Process>

The nitrogen-doped titanium oxide layer of the stent (N:TiO$_2$) was irradiated with a femtosecond pulse laser (1 sec/10$^{-15}$) under the operating conditions of the following Table 1 using an ultra-short femtosecond pulsed laser device (Light Conversion, Vilnius, LIT) equipped with a beam expander (CVI Laser Optics, New Mexico, USA), thereby manufacturing a stent (N:TiO$_2$-FSL) in which femtosecond laser processing was performed on the nitrogen-doped titanium oxide layer.

TABLE 1

| | |
|---|---|
| Power (W) | 6 |
| Wave length (nm) | 1,030 |
| Focal length (mm) | 40 |
| Working distance (mm) | 37.5 |
| Numerical aperture | 0.14 |
| Depth of focus (μm) | 14 |

<Drug Coating Process Using Electrospinning>

First, tacrolimus (TCL) as a drug and acetonitrile as a solvent were prepared. 0.006 mmol of tacrolimus was mixed with the acetonitrile solution so as to have a concentration of 0.8 mg/ml to prepare a mixed drug solution.

The mixed drug solution was electrospun on a stent (N:TiO$_2$-FSL) surface under the operating conditions of the following Table 2 to manufacture a tacrolimus drug-eluting stent (N:TiO$_2$-FSL-TCL) in which the femtosecond laser-processed nitrogen-doped titanium oxide layer was coated with tacrolimus.

TABLE 2

| | |
|---|---|
| Applied voltage (kV) | 5 |
| Air pressure (kgf/cm$^2$) | 6 |
| Distance from nozzle to stent (cm) | 12 |
| Spray speed (μl/min) | 50 |

Then, each of the water contact angles of the surfaces of the initial stent (BMS), the stent (N:TiO$_2$) coated with a titanium oxide layer, and the tacrolimus drug-eluting stent (N:TiO$_2$-FSL-TCL) was measured, and the results are shown in Table 4. In addition, the total tacrolimus loading amount and the tacrolimus elution delay characteristic of the tacrolimus drug-eluting stent (N:TiO$_2$-FSL-TCL) were evaluated, and each of the results is shown in FIGS. 5 and 6. Here, the total tacrolimus loading amount and the tacrolimus elution delay characteristic were measured by the following method. An elution test was performed at a rotation speed of 100 rpm and an elution temperature of 37° C. using 3 ml of a phosphate buffer saline (PBS) (pH 7.4), then, an elution solution was taken every day (every 24 hours), and high performance liquid chromatography (HPLC) was used to perform measurement at a wavelength of 213 nm to calculate the elution amount.

Example 2

The process was performed in the same manner as in Example 1, except that in the process of forming a nitrogen-doped titanium oxide layer, the reaction was performed until the average thickness of the nitrogen-doped titanium oxide layer was 0.1 μm.

Example 3

The process was performed in the same manner as in Example 1, except that in the process of coating a drug using electrospinning, cosolvents including acetone (boiling point: 56° C.) and acetonitrile (boiling point: 82° C.) at a weight ratio of 100:50 were used instead of the solvent.

Example 4

The process was performed in the same manner as in Example 1, except that in the process of coating a drug using electrospinning, cosolvents including acetonitrile (boiling point: 82° C.) and toluene (boiling point: 110° C.) at a weight ratio of 100:50 were used instead of the solvent.

Example 5

The process was performed in the same manner as in Example 1, except that in the process of coating a drug using electrospinning, cosolvents including tetrahydrofuran (boiling point: 66° C.) and toluene (boiling point: 110° C.) at a weight ratio of 100:50 were used instead of the solvent.

Example 6

The process was performed in the same manner as in Example 1, except that in the process of coating a drug using electrospinning, cosolvents including acetonitrile (boiling point: 82° C.) and benzene (boiling point: 80° C.) at a weight ratio of 100:50 were used instead of the solvent.

Comparative Example 1

The process was performed in the same manner as in Example 1, except that the mixed drug solution was electrospun on the nitrogen-doped titanium oxide layer without performing the femtosecond laser processing process to manufacture a tacrolimus drug-eluting stent (N:TiO$_2$-TCL) in which the nitrogen-doped titanium oxide layer was coated with tacrolimus.

Comparative Example 2

The process was performed in the same manner as in Example 3, except that the mixed drug solution was electrospun on the nitrogen-doped titanium oxide layer without performing the femtosecond laser processing process to manufacture a tacrolimus drug-eluting stent (N:TiO$_2$-TCL) in which the nitrogen-doped titanium oxide layer was coated with tacrolimus.

Experimental Example 1

<Drug Release Characteristic Evaluation Depending on Solvent in Electrospinning>

The tacrolimus drug-eluting stents (N:TiO$_2$-FSL-TCL) manufactured in Examples 1 and 3 to 6 were substantially the same except a difference in the kinds of solvents of the mixed drug solution used in the electrospinning in the process of coating a drug using electrospinning, and the total tacrolimus loading amounts and the tacrolimus elution delay characteristics thereof were evaluated.

As a result, in Examples 3 to 5 using the cosolvents including different solvents having a boiling point difference of 25° C. or more, the total loading amount was more improved by about 5% than that of Example 1 using a single solvent. In particular, the tacrolimus elution delay characteristics of Examples 3 to 5 were more improved by about 7% than that of Example 1. However, Example 6 using the cosolvents including different solvent from each other but having a boiling point difference of less than 25° C., specifically a boiling point difference of about 2° C., did not show any significant effect as in Examples 3 to 5, and is in a substantially equivalent degree and does not substantially show any solvent effect difference from Example 1.

In addition, as in Comparative Example 2, even when cosolvents having a boiling point difference of 25° C. or more were used, the femtosecond laser-unprocessed drug-eluting stent (N:TiO$_2$-TCL) did not show the effect of improving a drug release characteristic by the cosolvents in a significant degree.

Therefore, it was found that the effect is shown when the mixed drug solution including the cosolvents having a boiling point difference of 25° C. or more and the tacrolimus drug was electrospun on the femtosecond laser-processed nitrogen-doped titanium oxide layer.

Experimental Example 2

<Drug Release Characteristic Evaluation Depending on Average Thickness of Titanium Oxide Layer>

The tacrolimus drug-eluting stents (N:TiO$_2$-FSL-TCL) manufactured in Examples 1 and 2 were substantially the same except a difference in the average thicknesses of the nitrogen-doped titanium oxide layers, and the total tacrolimus loading amounts and the tacrolimus elution delay characteristics thereof were evaluated.

As a result, the total tacrolimus loading amount of Example 1 was more improved by about 12% than that of Example 2. In addition, the tacrolimus elution delay characteristic of Example 1 was more improved by about 6% than that of Example 2. Such results are considered to be due to the fact that the micropores and fine irregularities formed by the femtosecond laser processing secured structure stability so as not to destroy the titanium oxide layer structure.

Experimental Example 3

<Surface Characteristic Evaluation Right after Each Process>

FIG. 3 is scanning electron microscope (SEM) images for each of the surfaces of the initial stent (BMS), the stent (N:TiO$_2$) coated with a nitrogen-doped titanium oxide layer, and the stent (N:TiO$_2$-FSL) in which femtosecond laser processing was performed on a nitrogen-doped titanium oxide layer, in Example 1.

As shown in FIG. 3, it was confirmed that a plurality of micropores and fine irregularities were formed by irradiation of the femtosecond pulse laser on the nitrogen-doped titanium oxide layer.

Experimental Example 4

<Evaluation of Water Contact Angle>

The water contact angle of each of the surfaces of the initial stent (BMS), the stent (N:TiO$_2$) coated with a nitrogen-doped titanium oxide layer, and a stent (N:TiO$_2$-FSL) in which femtosecond laser processing was performed on a nitrogen-doped titanium oxide layer was measured, respectively, in Example 1 to evaluate a hydrophilicity degree of each surface.

As a result, as shown in FIG. 4, the water contact angles of the initial stent (BMS) was measured as 72.8°±5.37, the water contact angle of the stent (N:TiO$_2$) coated with a nitrogen-doped titanium oxide layer was measured as 18.3°±5.52, and the stent (N:TiO$_2$-FSL) in which femtosecond laser processing was performed on a nitrogen-doped titanium oxide layer was measured as 132.5°±6.82.

When the femtosecond laser processing was performed on the nitrogen-doped titanium oxide layer therefrom, it was confirmed that the hydrophobicity and the surface roughness of the surface were significantly increased, and then when the titanium oxide layer was coated with the tacrolimus drug by electrospinning, physical binding between the titanium oxide layer and the electrospinning between drugs may be further improved.

Experimental Example 5

<Evaluation of Total Tacrolimus Loading Amount and Elution Delay Characteristic>

The total tacrolimus loading amounts (mass unit) and the tacrolimus elution delay characteristics of the tacrolimus drug-eluting stent (N:TiO$_2$-FSL-TCL) manufactured in Example 1 and the tacrolimus drug-eluting stent (N:TiO$_2$-TCL) manufactured in Comparative Example 1 were evaluated.

As a result, as shown in FIG. 5, it was confirmed that the total tacrolimus loading amount of Example 1 was significantly more improved by about 40% or more than that of the Comparative Example 1. This is considered as an effect due to the fact that the femtosecond laser processing was performed on the nitrogen-doped titanium oxide layer.

In addition, as shown in FIG. 6, a similar result is shown in the tacrolimus elution delay characteristic also. Specifically, it was confirmed that the average release rate of the drug during the first day $((R_{1d}/R_A)/t_{1d})$ of Example 1 was 0.40, while the average release rate of the drug during the first day $((R_{1d}/R_A)/t_{1d})$ of Comparative Example 1 was 0.61. In addition, it was confirmed that the cumulative release amount for 7 days $(R_{7d}/R_A)$ of Example 1 was 0.72, while the cumulative release amount for 7 days $(R_{7d}/R_A)$ of Comparative Example 1 was 0.82.

The invention claimed is:

1. A manufacturing method of a tacrolimus drug-eluting stent, the method comprising:
   a) forming a nitrogen-doped titanium oxide layer on a stent surface,
   b) irradiating the titanium oxide layer with a femtosecond pulse laser to perform femtosecond laser processing, and c) electrospinning an electrospinning mixed solution including a tacrolimus drug and a solvent on the femtosecond laser-processed titanium oxide layer, wherein in c), the solvent is cosolvents including a first solvent and a second solvent, and the first solvent and the second solvent have a boiling point difference of 25° C. or more and each boiling point of the two solvents is 120° C. or less.

2. The manufacturing method of a tacrolimus drug-eluting stent of claim 1, wherein in a), the titanium oxide layer has an average thickness of 0.2 to 2 μm.

3. The manufacturing method of a tacrolimus drug-eluting stent of claim 1, wherein in c), the boiling point of the first solvent is lower than the boiling point of the second solvent, and a weight ratio of the first solvent to the second solvent is 100:30 to 80.

4. The manufacturing method of a tacrolimus drug-eluting stent of claim 1, wherein in c), the electrospinning mixed solution does not include a polymer.

5. The manufacturing method of a tacrolimus drug-eluting stent of claim 1, wherein in b), the femtosecond laser-processed titanium oxide layer satisfies the following Relation 1:

$$\theta_F/\theta_0 \geq 5 \qquad \text{[Relation 1]}$$

wherein $\theta_F$ is a water contact angle to the femtosecond laser-processed titanium oxide layer and $\theta_0$ is a water contact angle to the femtosecond laser-unprocessed titanium oxide layer.

6. A manufacturing method of a tacrolimus drug-eluting stent, the method comprising:

a) forming a nitrogen-doped titanium oxide layer on a stent surface, b) irradiating the titanium oxide layer with a femtosecond pulse laser to perform femtosecond laser processing, and c) electrospinning an electrospinning mixed solution including a tacrolimus drug and a solvent on the femtosecond laser-processed titanium oxide layer, wherein in b), the femtosecond laser-processed titanium oxide layer satisfies the following Relation 1:

$$\theta_F/\theta_0 \geq 5 \qquad \text{[Relation 1]}$$

wherein $\theta_F$ is a water contact angle to the femtosecond laser-processed titanium oxide layer and $\theta_0$ is a water contact angle to the femtosecond laser-unprocessed titanium oxide layer.

* * * * *